United States Patent [19]

Bingham et al.

[11] 4,120,856

[45] Oct. 17, 1978

[54] PROCESS FOR THE PREPARATION OF 3-FLUOROBENZODIAZEPINES

[75] Inventors: Elena Maria Bingham, Wilmington, Del.; William Joseph Middleton, Chadds Ford, Pa.

[73] Assignee: E. I. Du Pont de Nemours and Company, Wilmington, Del.

[21] Appl. No.: 854,261

[22] Filed: Nov. 23, 1977

Related U.S. Application Data

[63] Continuation of Ser. No. 687,318, May 26, 1976, which is a continuation-in-part of Ser. No. 597,502, Jul. 31, 1975, abandoned.

[51] Int. Cl.$^2$ .................. C07D 243/26; C07D 487/04

[52] U.S. Cl. .................. 260/239.3 D; 260/308 R; 424/244; 424/269

[58] Field of Search .................. 260/239.3 D, 308 R

[56] References Cited

U.S. PATENT DOCUMENTS

| 3,371,085 | 2/1968 | Reeder et al. ................. 260/239.3 D |
| 3,914,265 | 10/1975 | Middleton ........................ 260/239.1 |

*Primary Examiner*—Henry R. Jiles
*Assistant Examiner*—Robert T. Bond

[57] ABSTRACT

3-Fluorobenzodiazepines, such as 3-fluoro-1,3-dihydro-1-methyl-7-chloro-5-phenyl-2H-1,4-benzodiazepin-2-one, useful as tranquilizers, muscle relaxants, and sedatives.

1 Claim, No Drawings

PROCESS FOR THE PREPARATION OF 3-FLUOROBENZODIAZEPINES

This is a continuation of application Ser. No. 687,318, filed May 26, 1976, which in turn is a continuation-in-part of Ser. No. 597,502, filed July 31, 1975, now abandoned.

BACKGROUND

This invention relates to benzodiazepine tranquilizers.

Bell, in U.S. Pat. No. 3,198,789, discloses 3-chloro derivatives of benzodiazepines as starting materials in the preparation of benzodiazepines with an amino group in the 3-position. He states that the chlorine at the 3-position is very reactive, the compounds reacting at room temperature or below; also that one skilled in the art of organic chemistry would realize that the analogous 3-bromo and 3-iodo compounds could be used in place of the 3-chloro.

Bell, in U.S. Pat. No. 3,296,249, discloses a sequence of reactions that includes the preparation of 3-halo-5-monocyclic-aryl-1,3-dihydro-2H-1,4-benzodiazepin-2-one from the unsubstituted N oxide. These are intermediates for making the 3-hydroxy compounds. The term halo is not defined. He also discloses that the 3-hydroxy compounds can be converted to their corresponding 3-chloro derivatives by treating with an inorganic acid halide, such as thionyl chloride or phosphorous pentachloride. Thionyl fluoride has been unsuccessful as a fluorinating agent with alcohols. [Weichert, K. and Hoffmeister, R., J. Prakt Chem., 10, 290–302 (1960)]

Bell et al., in U.S. Pat. No. 3,296,251, disclose 3-halo-benzodiazepines as intermediates for preparing 3-mercapto-benzodiazepines, and states that a halogen at position 3 is very active: reacting at room temperature with mercapto compounds.

Fryer et al., in U.S. Pat. No. 3,371,083 disclose benzodiazepines substituted in the 3-position with chlorine, bromine, or iodine, which are useful as intermediates.

Fryer et al., in U.S. Pat. No. 3,371,084 disclose 3-halo-1,4-benzodiazepin-2-ones useful as intermediates, where the halogen is preferentially bromine, chlorine, or iodine. Fluorine is not disclosed.

Sternbach, in U.S. Pat. No. 3,450,695, discloses 3-halo-benzodiazepines as intermediates made by treatment of the 3-hydroxy compound with a halogenating agent, such as an inorganic acid halide.

Sternbach et al., in J. Med. Chem., 8, 815 (1965), describe the preparation and some of the reactions of 7-chloro-1,3-dihydro-5-(2-fluorophenyl)-2H-1,4-benzodiazepin-2-one.

Bell and Childress, in J. Org. Chem., 27, 1691 (1962), disclose 3,7-dichloro-5-phenyl-1,3-dihydro-2H-1,4-benzodiazepin-2-one prepared by reacting the 3-hydroxy compound with thionyl chloride. This 3-chloro derivative, however, was described as extremely reactive: mere warming in alcohol caused decomposition.

Stempel et al., in U.S. Pat. No. 3,321,467, disclose 3-halo-1,4-benzodiazepin-2-one 4-oxides prepared by treating 2-halo-quinazoline 3-oxides with a suitable inorganic base. The halogen is defined as chlorine, bromine, or fluorine; preferably chlorine. The fluorine derivative is not specifically described or exemplified.

No known reference discloses the 3-fluorobenzodiazepines of this invention. Several references teach 3-halo derivatives; mentioning chlorine, bromine, and iodine and specifically exemplifying chlorine. The consensus of the prior art is that 3-halo-benzodiazepines are too reactive and unstable to be practically useful as pharmaceuticals.

There are fundamental differences, however, between chlorine, bromine, and iodine — the halogens disclosed in the prior art — and fluorine. It is known in organic chemistry that fluorine is a separate and distinct entity in comparison to chlorine, bromine, and iodine; and is different to such a degree that fluorocarbon chemistry has achieved a completely separate status. Differences between these elements are many. For example:

Fluorine has no low-lying d-orbitals for backbonding as do chlorine, bromine, and iodine, thus leading to less polarizable bonds.

Chlorine, bromine, and iodine can be found in positive valence states ($ClO_4$, $BrO_3$, and $I_2O_5$) whereas fluorine cannot.

The well-known "haloform" reaction occurs with bromine, chlorine, and iodine, but not with fluorine.

Metal-fluorides differ from metal-chlorides, -bromides, and -iodides: for example, the solubility of silver fluoride in water is one million times greater than the solubility of silver-chloride, -bromide, and -iodide.

Many authorities have noted and recognized the differences between fluorine and halogens. For example:

Sheppard and Sharts, in "Organic Chemistry", W. A. Benjamin (1969) devote the first two chapters to the differences between fluorine and the halogens.

Cotton and Wilkinson, in "Advanced Inorganic Chemistry", Interscience (1962) discuss fluorine compounds in Chapter 14, and chlorine, bromine, and iodine compounds in Chapter 22.

Roberts and Caserio in "Basic Principles of Organic Chemistry", W. A. Benjamin (1964) in Chapter 17, covers chlorine, bromine, and iodine compounds under headings "Alkyl Halides", "Alkenyl Halides", "Cycloalkyl Halides", and "Polyhalogen Compounds". Fluorine compounds are covered under "Fluorinated Alkanes."

Accordingly, under modern chemical practice, fluorine has acquired a separate status, and therefore it is incorrect to conclude that mention of the halogens chlorine, bromine, or iodine necessarily suggests fluorine.

In marked contrast to the 3-chloro-benzodiazepines of the prior art, which Bell and Childress said were too unstable to even give satisfactory analytical results, the 3-fluoro-benzodiazepines of this invention are surprisingly stable against hydrolysis by both aqueous acids and bases, making them especially suitable as pharmaceuticals.

A number of benzodiazepines are well-known useful tranquilizers, muscle-relaxants, and sedatives. Metabolic studies with several of these compounds, including diazepam [Schwartz, M. A. et al., J. Pharmacol. Exp. Ther., 149, 423 (1965)], flurazepam [Schwartz, M. A. and Postma, E. J Pharm. Sci., 59, 1800 (1970)], and nitrazepam [Rieder, J. and Wendt, G., "Benzodiazepines", Garattini, S., Mussini, E., and Randall, L. O., eds., 799, Raven Press, New York (1973)], have shown that they are metabolized in man and other animals by oxidative attack at the 3-position. Substitution with fluorine in this 3-position appears to retard this metabolic pathway, resulting in more potent activity for the 3-fluoro derivatives of this invention.

SUMMARY

According to this invention there is provided compounds of formula I, processes for making them, pharmaceutical compositions containing them, and methods of using them as tranquilizers, muscle-relaxants, and sedatives in mammals.

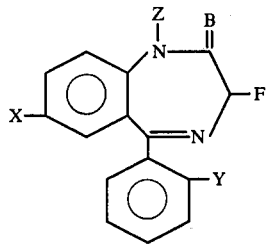

Formula I where
X is Cl, Br, $NO_2$ or $CF_3$;
Y is H, Cl, Br or F;
Z = H, hydrocarbyl of 1–4 carbons, $-CH_2CF_3$, $-CONHR$, $-CH_2CH_2NR_2$, or $-CH_2CH_2NR_2 \cdot A$, where R = alkyl of 1–4 carbons, and A is a pharmaceutically suitable acid;
B = O; or
B and Z together = $=N-N=C(R')-$ where $R'$ = H, or $C_1-C_4$ alkyl.

DETAILED DESCRIPTION

Preferred Compounds

Compounds preferred for their activity are those where, independently:
B = O;
X = Cl;
Z = H;
Z = $C_1-C_3$ alkyl;
X = Cl and Z = H;
X = Cl and Z = $C_1-C_3$ alkyl.

More preferred are those compounds where:
X = Cl or Br;
Y = H, Cl, or F;
Z = H, $-CH_3$, or $-CH_2CH_3$; and
B = O.

Most preferred are those compounds where:
X = Cl or Br;
Y = H or F;
Z = $CH_3$; and
B = O.

Specifically preferred are the following compounds:

3-fluoro-1,3-dihydro-1-methyl-7-chloro-5-phenyl-2H-1,4-benzodiazepin-2-one;
3-fluoro-1,3-dihydro-1-methyl-7-chloro-5-(2'-fluorophenyl)-2H-1,4-benzodiazepin-2-one;
3-fluoro-1,3-dihydro-1-methyl-7-bromo-5-phenyl-2H-1,4-benzodiazepin-2-one;
3-fluoro-1,3-dihydro-7-bromo-5-phenyl-2H-1,4-benzodiazepine-2-one.

The term hydrocarbyl of 1–4 carbons includes alkyl groups such as methyl, ethyl, isopropyl, and isobutyl; cycloalkyl containing groups such as cyclopropyl and cyclopropylmethyl; and alkenyl groups such as allyl and 2-butenyl.

Pharmaceutically suitable acids (A) include those such as HCl, $H_2SO_4$, $HNO_3$, $H_3PO_4$, acetic, tartaric, citric, maleic, fumaric, and the like.

Synthesis

These compounds are made by the following general method: Contacting a 3-hydroxybenzodiazepine with a dialkylaminosulfur trifluoride at about $-80°$ to $10°$ C. under substantically anhydrous conditions:

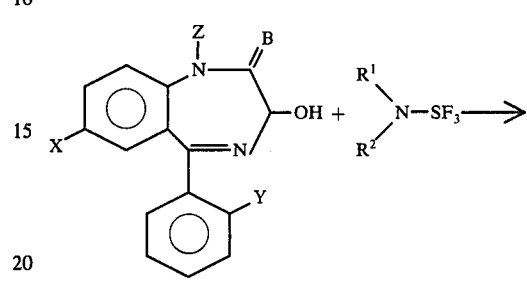

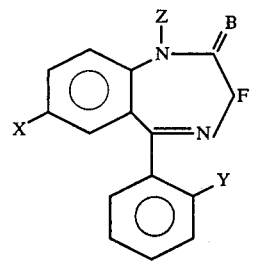

B, X, Y and Z are as previously defined. $R^1$ and $R^2$ individually are a primary alkyl group of 1–4 carbons or taken together are $-(CH_2)_4-$ or $-(CH_2)_5-$.

It is preferred to operate in the temperature range of $-80°$ to $-10°$ C. when Z is hydrogen; and $-80°$ to $+10°$ C. when Z is other than hydrogen.

The dialkylaminosulfur trifluorides decompose very readily on contact with water, so water should be excluded from the reaction as much as possible. "Substantially anhydrous conditions" is therefore intended to mean that the amount of water present is so small that it will not significantly decompose the dialkylaminosulfur trifluoride, consequently, not interfering with the reaction.

The reaction can be carried out by dissolving or suspending the hydroxyl compound in an inert solvent and then adding the fluorinating agent. An inert solvent is one that does not enter into the reaction and includes diethyleneglycol dimethyl ether (diglyme), pentane, trichlorofluoromethane, and the like; preferred are chlorinated solvents that are liquid at the reaction temperature, such as methylene chloride and chloroform. The product can be isolated from the reaction mixture and purified by conventional means; for example, the reaction mixture can be poured into water, the organic layer separated and washed with water, and then evaporated to dryness. The resulting crude 3-fluorobenzodiazepines can then be further purified by recrystallization from suitable solvents.

The 3-hydroxy-benzodiazepines used in this reaction are either known compounds or can be prepared by methods described in the literature. For example: Bell and Childress, *J. Org. Chem.*, 27, 1691 (1962); Bell et al., *Tetrahedron Lett.*, p. 2889 (1965); Bell et al., *J. Org. Chem.*, 33, 216 (1965); Miyadera et al., *J. Med. Chem.*, 14, 520 (1971); Ning et al., *J. Org. Chem.*, 38, 4206

(1973); Sankyo Company, German Pat. No. 1,812,252 (1969); 1,952,201 (1970); 1,954,065 (1970); Schlager, *Tetrahedron Lett.*, p. 4519 (1970); Stempel et al., *J. Org. Chem.*, 32, 4267 (1967); Stempel et al., *J. Org. Chem.*, 30, 4267 (1965).

The dialkylaminosulfur trifluorides can be prepared by the reaction of a dialkylaminotrimethylsilane with sulfur tetrafluoride at a low temperature in an inert solvent. Diethylaminosulfur trifluoride, dimethylaminosulfur trifluoride, and pyrrolidinosulfur trifluoride can be prepared by this method. When this reaction is conducted in trichlorofluoromethane at −70° C., high yields of a product of high purity are obtained because the only appreciable by-product is fluorotrimethylsilane, an easily separated low boiling material. These three trifluorides are stable products that can be distilled and stored in plastic bottles at room temperature.

Preparation and use of these fluorinating agents is described by Middleton, W. J., *J. Org. Chem.*, 40, 574 (1975) and U.S. Pat. No. 3,914,265 issued Oct. 21 1975.

DIETHYLAMINOSULFUR TRIFLUORIDE

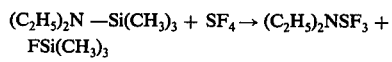

A dry 1-l. four-necked round-bottomed flask is equipped with a thermometer (−100° to 50°), a solid carbon dioxide-cooled reflux condenser (protected from the atmosphere through a drying tube), a gas inlet tube above the liquid level, and a magnetic stirrer. The apparatus is flushed with dry nitrogen, and 300 ml of trichlorofluoromethane is added to the flask. As the nitrogen atmosphere is maintained, the trichlorofluoromethane is cooled to −70° by means of a solid carbon dioxide-acetone bath and 119 g (1.1 mole) of sulfur tetrafluoride is added from a cylinder through the gas inlet tube. The gas inlet tube is then replaced with a 250-ml pressure-equalized dropping funnel charged with a solution of 145 g (1 mole) of N,N-diethylaminotrimethylsilane in 90 ml trichlorofluoromethane. This solution is added dropwise, with stirring, to the sulfur tetrafluoride solution at a rate slow enough to keep the temperature of the reaction mixture below −60° (about 40 minutes). The cooling bath is removed, and the reaction mixture is allowed to warm spontaneously to room temperature. The condenser is replaced with a simple distillation head, and the solvent (bp 24°) and by-product fluorotrimethylsilane (bp 17°) are distilled off into a well cooled receiver by warming the reaction mixture gently to 45° by means of a heating mantle. The yellow to dark brown residual liquid is transferred and distilled at reduced pressure through a spinning band column to give 129–145 g (80–90%) of diethylaminosulfur trifluoride as a light yellow liquid, bp 46–47 (10 mm).

An alternate method for making benzodiazepinones where Z is other than hydrogen is contacting a 3-fluorobenzodiazepinone with sodium hydride at about 0°–30° C. in an inert solvent such as tetrahydrofuran, 1,2-dimethoxymethylene, or diethylether, to produce the sodium salt; then contacting this, in the same solvent without isolation, with an alkylating agent to produce a 1-alkyl-3-fluorobenzodiazepinone. The alkylating agent can have the formula $QZ^1$ where $Z^1$ has the same value as previously defined for Z but excludes hydrogen; and Q is I, Cl, Br, $CF_3SO_2O-$, $FSO_2O-$, $CCl_3SO_2O-$, or $Z^1OSO_2O-$.

4-Fluorotriazolobenzodiazepines, such as 4-fluoro-8-chloro-1-methyl-6-phenyl-4H-s-triazolo[4.3-*a*][1,4]-benzodiazepine for example, can be prepared as follows: by treating a solution of 8-chloro-4-hydroxy-1-methyl-4H-s-triazolo[4.3-*a*][1,4]benzodiazepine in methylene chloride with diethylaminosulfur trifluoride at −70°, warming the reaction mixture to −20°, and then pouring it into cold water. 4-Fluoro-8-chloro-1-methyl-6-phenyl-4H-s-triazolo[4.3-*a*][1,4]benzodiazepine can be isolated from the organic layer by evaporation of the solvent. The particular 4-hydroxy compound shown here can be prepared as described in U.S. Pat. No. 3,907,820 (1975) (assigned to Takeda Chemical Industries, Ltd.).

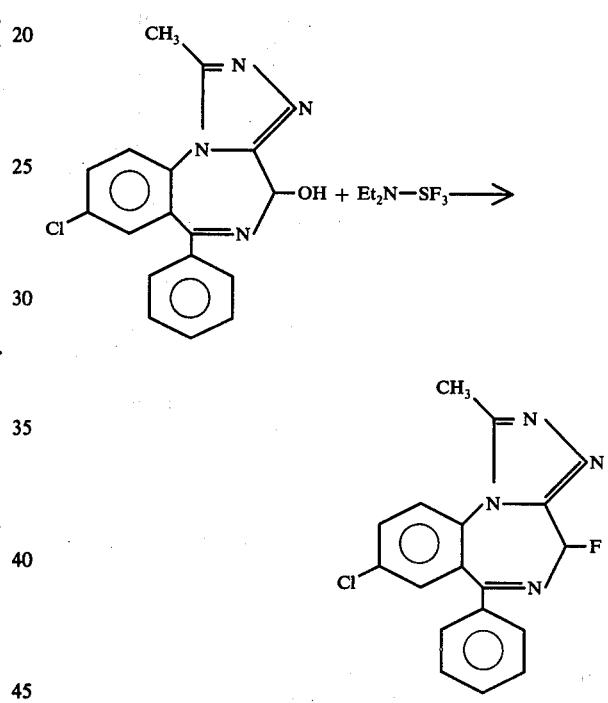

The following examples further illustrate how to make the compounds of this invention. Parts are by weight and temperatures are in degrees Centigrade unless otherwise specified.

EXAMPLE 1

3-Fluoro-1,3-dihydro-7-chloro-5-phenyl-2H-1,4-benzodiazepin-2-one

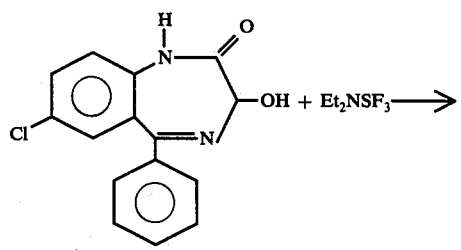

-continued

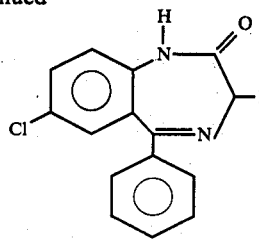

A well stirred suspension of 10 g (0.03 mol) of 3-hydroxy-1,3-dihydro-7-chloro-5-phenyl-2H-1,4-benzodiazepin-2-one and 500 ml of methylene chloride was cooled to −70°. Diethylaminosulfur trifluoride (25 ml, 0.2 mol) was then added dropwise with exclusion of moisture and air. On completion of the addition the dry-ice acetone bath was removed, the contents of the flask were allowed to warm up in about 25 minutes to −10° and the reaction then immediately quenched by pouring into a beaker containing 400–500 ml of ice water. (If the reaction mixture is allowed to warm to 25°, none of the desired product is obtained.) Vigorous stirring of the ice water mixture continued for 7 to 10 minutes. The organic layer was separated, dried over MgSO$_4$ and evaporated under reduced pressure to give a light orange powder. The product was dissolved in hot benzene, treated with decolorizing charcoal and filtered hot. On addition of heptane to the benzene solution, followed by cooling in ice, 3-fluoro-1,3-dihydro-7-chloro-5-phenyl-2H-1,4-benzodiazepin-2-one crystallized out as a white powder, 8.19 g (82%): mp 190°–192° (decom.); $^{19}$F nmr (DMSO-d$_6$) δ −161.5 ppm (d, d, J = 56, 4 Hz, 1H), $^1$H nmr (DMSO-d$_6$) δ 7.2–7.8 (m, 8H), δ 5.72 (d, J = 56 Hz, 1H), δ 11.0 ppm (N-H).

| Anal. Calcd for C$_{15}$H$_{10}$ClN$_2$OF: | C, | 62.40; | H, | 3.49; | N, 9.70 |
|---|---|---|---|---|---|
| Found: | C, | 62.77; | H, | 3.97; | N, 9.29 |
| | | 62.72 | | 4.01 | 9.31 |

EXAMPLE 2

3-Fluoro-1,3-dihydro-1-methyl-7-chloro-5-phenyl-2H-1,4-benzodiazepin-2-one

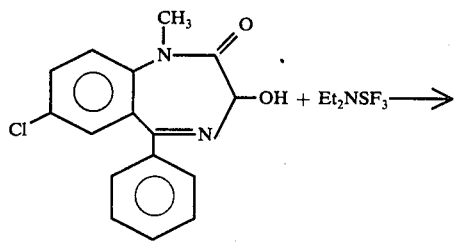

A. A solution of 12.1 g (0.04 mol) of 3-hydroxy-1,3-dihydro-1-methyl-7-chloro-5-phenyl-2H-1,4-benzodiazepin-2-one in 25 ml of anhydrous methylene chloride was added dropwise over a period of 15 min. to a stirred solution of 12.6 ml (0.1 mol) of diethylaminosulfur trifluoride in 300 ml of anhydrous methylene chloride cooled to −70°. The reaction mixture was allowed to warm slowly over a period of 45 min. to 5° and then poured into 500 ml of ice and water. The lower organic layer was separated, washed with water, dried over anhydrous magnesium sulfate, and evaporated to dryness under reduced pressure to give 10.9 g (90% yield) of crude product as a light yellow solid residue. Recrystallization from heptane gave 8.48 g (70% yield) of 3-fluoro-1,3-dihydro-1-methyl-7-chloro-5-phenyl-2H-1,4-benzodiazepin-2-one as colorless crystals: mp 138°–140°; $^{19}$F nmr (CCl$_3$D) δ −161.7 ppm (d, J = 57 Hz); $^1$H nmr (CCl$_3$D) δ 3.43 ppm (s, 3H), 5.54 ppm (d, J = 57 Hz, 1H), 7.5 ppm (m, 8H).

Anal. Calcd for C$_{16}$H$_{12}$ClFN$_2$O: C, 63.47; H, 4.00; F, 6.28; N, 11.71. Found: C, 63.53; H, 4.21; F, 6.21; N, 11.50.

B. The same compound can be prepared by the alternate method as follows:

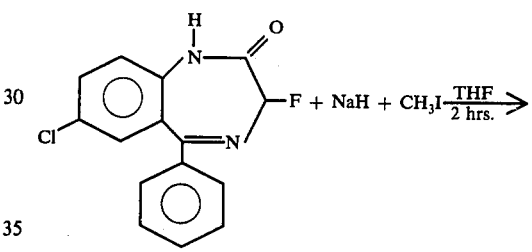

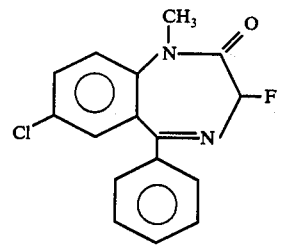

To a well stirred solution of 3.0 g (0.01 mol) of 3-fluoro-1,3-dihydro-7-chloro-5-phenyl-2H-1,4-benzodiazepin-2-one, 75 ml of dry THF and 25.56 g (0.18 mol, 11.2 ml) of methyl iodide was added a suspension of 0.48 g (0.02 mol) of sodium hydride in 20 ml of THF. There was an immediate evolution of hydrogen. The contents of the flask were stirred under a nitrogen atmosphere for exactly 2 hours. The product mixture was poured into approximately 100 ml of water and methylene chloride added to extract the product. The organic layer was separated and washed twice with ca. 50 ml portion of fresh water, and then allowed to dry over magnesium sulfate. Evaporation of the solvent under reduced pressure gave 1.38 g of a yellow crystalline material. Recrystallization from hot heptane gave 0.97 g of an off-white powder identified as 3-fluoro-1-(N-methyl)-7-chloro-5-phenyl-1,4-benzodiazepin-2-one: $^1$H nmr (DMSO-d$_6$): δ 7.2–7.72 ppm (m, 8H), δ 5.8 ppm (d, 1H, 56 Hz), δ 3.37 (m, 3H, N-methyl); $^{19}$F nmr (DMSO-d$_6$) δ −160.14 ppm (d, J = 56 Hz).

EXAMPLE 3

3-Fluoro-1,3-dihydro-7-chloro-5-(2-fluorophenyl)-2H-1,4-benzodiazepin-2-one

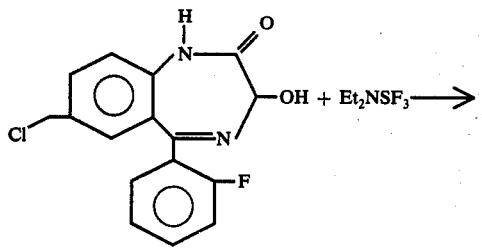

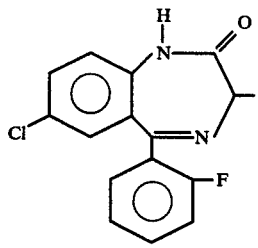

A well stirred suspension of 3.0 g (0.01 mole) of 3-hydroxy-1,3-dihydro-7-chloro-5-(2-fluorophenyl)-2H-1,4-benzodiazepin-2-one in 150 ml of methylene chloride was cooled to −70°, and 7.5 ml (0.06 mol) of diethylaminosulfur trifluoride was added dropwise over a period of 10 min. The reaction mixture was then allowed to warm slowly over a period of 26 min. to −10° and then poured into 200 ml of ice water. The organic layer was separated, dried over MgSO$_4$, and evaporated to dryness under reduced pressure to give 2.95 g (98%) of crude product. Recrystallization from benzene-heptane gave 2.00 g (67%) of 3-fluoro-1,3-dihydro-7-chloro-5-(2-fluorophenyl)-2H-1,4-benzodiazepin-2-one as off-white crystals: mp 206°–207° (dec); $^1$H nmr (DMSO-d$_6$) δ 5.95 ppm (d, J = 56 Hz, 1H), 7.47 ppm (m, 7H), 11.25 ppm (s, 1H); $^{19}$F nmr (DMSO-d$_6$) δ −162.0 ppm (d, J = 56 Hz, 1F) and δ −113.0 ppm (m, 1F).

Anal. Calcd for C$_{15}$H$_9$ClF$_2$N$_2$O: C, 58.74; H, 2.96; F, 12.39; N, 9.14. Found: C, 58.54; H, 3.21; F, 12.11; N, 8.98.

EXAMPLE 4

3-Fluoro-1,3-dihydro-1-ethyl-7-chloro-5-phenyl-2H,-1,4-benzodiazepin-2-one

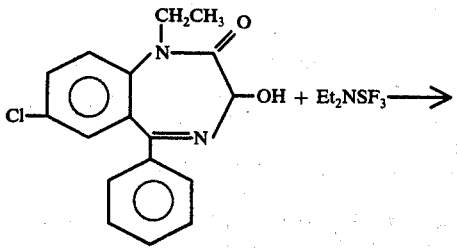

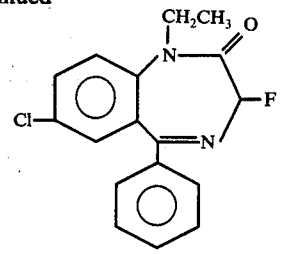

A solution of 3.5 g (0.01 mol) of 3-hydroxy-1,3-dihydro-1-ethyl-7-chloro-5-phenol-2H-1,4-benzodiazepin-2-one in 7 ml of anhydrous methylene chloride was added dropwise to a stirred solution of 3.53 ml (0.028 mol) of diethylaminosulfur trifluoride in 84 ml of anhydrous methylene chloride cooled to −70°. The reaction mixture was allowed to warm slowly to 5° and then poured into 150 ml of ice and water. The lower organic layer was separated, washed with water, dried over anhydrous magnesium sulfate, and evaporated to dryness under reduced pressure to give 2.84 g (90% yield) of crude product as light yellow crystals. Recrystallization from 200 ml of heptane gave 1.81 g (57% yield) of 3-fluoro-1,3-dihydro-1-ethyl-7-chloro-5-phenyl-2H-1,4-benzodiazepin-2-one: mp 156°–158°; $^1$H nmr (DMSO-d$_6$) δ 7.2–7.8 ppm (m, 8H), δ 5.85 ppm (d, 1H, J = 57 Hz), δ 3.5–4.38 (m, 2H, methylene protons on nitrogen), δ 1.02 (t, 3H).

Anal. Calcd for C$_{17}$H$_{14}$N$_2$ClF: C, 64.46; H, 4.46; F, 6.00; N, 8.84. Found: C, 64.46; H, 4.71; F, 6.57; N, 8.67.

EXAMPLE 5

3-Fluoro-1,3-dihydro-1-methyl-7-chloro-5-(2-fluorophenyl)-2H-1,4-benzodiazepin-2-one

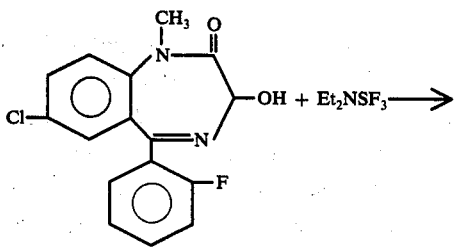

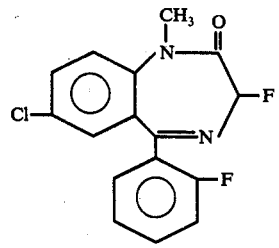

A solution of 1.4 g of 3-hydroxy-1,3-dihydro-1-methyl-7-chloro-5-(2-fluorophenyl)-2H-1,4-benzodiazepin-2-one in 10 ml of methylene chloride was added dropwise to a stirred solution of 1.5 ml of diethylaminosulfur trifluoride in 50 ml methylene chloride cooled to −70°. The reaction mixture was allowed to warm slowly to 5° and then poured into 100 ml of ice water. The lower organic layer was separated, washed with water, dried over anhydrous magnesium sulfate, and evaporated to dryness under reduced pressure. The residue was recrystallized from heptane to give 1.17 g of 3-fluoro-1,3- dihydro-1-methyl-7-chloro-5-(2-fluorophenyl)-2H-1,4-benzodiazepin-2-one as cream-colored crystals: mp 91°–95°; Hu 1H nmr (CCl$_3$D) δ 3.51 ppm (s, 3H), 5.66 ppm (d, J = 57 Hz, 1H) and 7.5 ppm (m, 7H).

Anal. Calcd for C$_{16}$H$_{11}$ClF$_2$N$_2$O$_2$: C, 59.91; H, 3.46; F, 11.85; N, 8.74. Found: C, 60.00; H. 3.57; F, 11.55; N, 8.69.

EXAMPLE 6

3-Fluoro-1-(allyl)-7-chloro-5-phenyl-2H-1,4-benzodiazepin-2-one

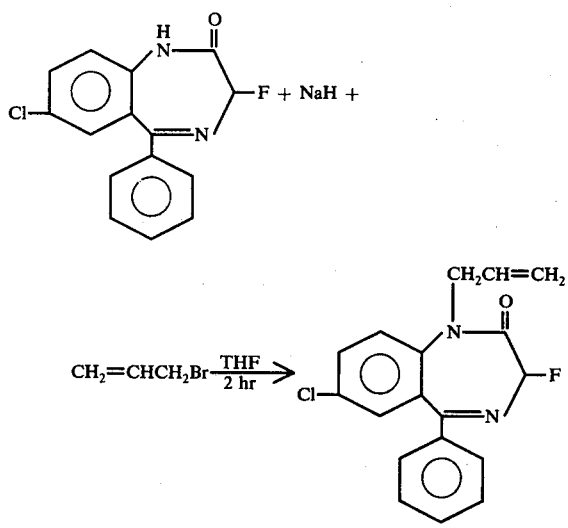

To a well stirred solution of 3.0 g (0.01 mol) of 3-fluoro-1,3-dihydro-7-chloro-5-phenyl-2H-1,4-benzodiazepin-2-one, 75 ml of dry THF and 21.78 g (0.18 mol) of 3-bromopropene, was added a suspension of 0.48 g (0.02 mol) of sodium hydride in 20 ml of THF. There was an immediate evolution of hydrogen. The contents of the flask were stirred under a nitrogen atmosphere for exactly two hours. The product mixture was poured into 100 ml of water and methylene chloride was added to extract the product. The organic layer was washed twice with 50 ml portions of water, and then allowed to dry over magnesium sulfate. Evaporation of the solvent under reduced pressure gave an orange gluey material which was recrystallized from 450 ml of hot heptane to give 1.42 g of 3-fluoro-1-(allyl)-7-chloro-5-phenyl-2H-1,4-benzodiazepin-2-one as a very pale orange powder: mp 138°–140°, $^1$H nmr (CDCl$_3$) δ 7.2–7.9 ppm (m, 8H), δ 5.6 ppm (d, J = 57.5 Hz, 1H), δ 4.85–5.95 ppm (m, 3H, olefinic), δ 4.58 ppm (2H, N—CH$_2$); $^{19}$F nmr (CDCl$_3$) δ 161.97 ppm.

Anal. Calcd for C$_{18}$H$_{14}$N$_2$ClF: C, 65.76; H, 4.29; F, 5.78; N, 8.52. Found: C, 66.06; H, 4.55; F, 5.46; N, 8.29.

EXAMPLE 7

3-Fluoro-7-bromo-1,3-dihydro-5-phenyl-2H-1,4-benzodiazepin-2-one

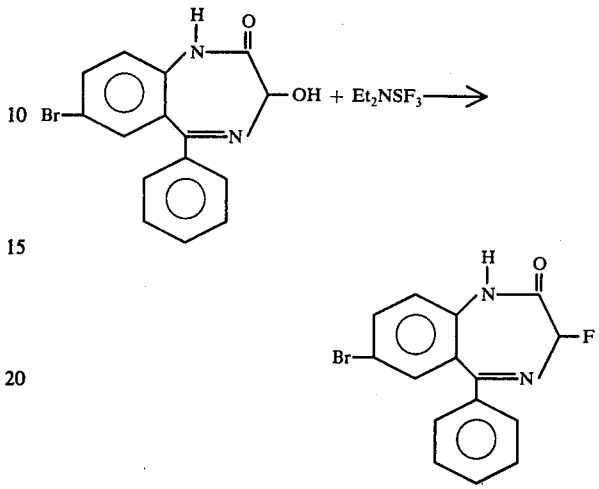

A well stirred suspension of 6.0 g (0.018 mole) of 7-bromo-1,3-dihydro-3-hydroxy-5-phenyl-2H-1,4-benzodiazepin-2-one in 250 ml methylene chloride was cooled to −70°, and 7.5 ml (0.06 mole) of diethylaminosulfur trifluoride was added dropwise. The reaction mixture was allowed to warm slowly to −10° over a period of 30 min., and held at −10° for 20 min., until most of the solid had dissolved. The reaction mixture was poured into 500 ml of ice water and stirred until the yellow color faded. The organic layer was separated, dried over MgSO$_4$, and evaporated to dryness under reduced pressure. The residue was dissolved in 300 ml of hot benzene and filtered hot. The filtrate was mixed with 400 ml hexane and cooled. The crystals that separated were collected on a filter, washed with hexane, and dried in air to give 5.28 g (88%) of 3-fluoro-7-bromo-1,3-dihydro-5-phenyl-2H-1,4-benzodiazepin-2-one as colorless crystals: mp 207°–209° (dec.); $^{19}$F nmr (acetone-d$_6$) δ −162.6 ppm (d, J = 57 Hz); $^1$H nmr (acetone-d$_6$) δ 5.86 ppm (d, J = 57 Hz, 1H), 7.2–8 ppm (m, 8H), 9.90 ppm (NH); ir (KBr) 5.84μ (C=O). A sample was dried in a vacuum oven for analysis.

Anal. Calcd for C$_{15}$H$_{10}$BrFN$_2$O: C, 54.07; H, 3.03; N, 8.41; F, 5.70. Found: C, 54.31; H, 3.17; N, 8.40; F, 5.62.

The 7-bromo-1,3-dihydro-3-hydroxy-5-phenyl-2H-1,4-benzodiazepin-2-one used in this preparation was prepared by the following procedure. A 10.0-g (0.03 mole) sample of 7-bromo-1,3-dihydro-5-phenyl-2H-1,4-benzodiazepin-2-one 4-oxide was added portionwise to 50 ml of trifluoroacetic anhydride, and the reaction mixture was stirred at room temperature for 2 hr. The suspended solid was collected on a filter, washed thoroughly with pentane, and dried in vacuum over potassium hydroxide pellets to give 12.8 g (99%) of 7-bromo-1,3-dihydro-5-phenyl-3-trifluoroacetoxy-2H-1,4-benzodiazepin-2-one as a white crystalline powder; mp 181°–183°; $^1$H nmr (DMSO-d$_6$) δ 6.28 ppm (s, 1H), 7.64 ppm (m, 8H), and 11.38 ppm (NH); $^{19}$F nmr (DMSO-d$_6$) δ −74.6 ppm (s).

Anal. Calcd for C$_{17}$H$_{10}$BrF$_3$N$_2$O$_3$: C, 47.79; H, 2.36; N, 6.56. Found: C, 47.66; H, 2.33; N, 6.26.

A suspension of 10 g (0.023 mole) of 7-bromo-1,3-dihydro-5-phenyl-3-trifluoroacetoxy-2H-1,4-benzodiazepin-2-one in a mixture of 130 ml ethanol and 130 ml of 5% aqueous sodium bicarbonate was stirred at room temperature (25°) for 20 hr. The suspended solid was collected on a filter, washed with water, and recrystallized from ethanol to give 6.5 g (85%) of 7-bromo-1,3-dihydro-3-hydroxy-5-phenyl-2H-1,4-benzodiazepin-2-one as colorless plates: mp 190°–192°; $^1$H nmr (DMSO-d$_6$) δ 4.86 ppm (1H), 6.27 ppm (1H, OH), 7.18–7.90 ppm (m, 8H).

Anal. Calcd for C$_{15}$H$_{11}$BrN$_2$O$_2$: C, 54.40; H, 3.35; N, 8.46. Found: C, 54.61; H, 3.51; N, 8.47.

EXAMPLE 8

3-Fluoro-7-bromo-1,3-dihydro-1-methyl-5-phenyl-2H-1,4-benzodiazepin-2-one

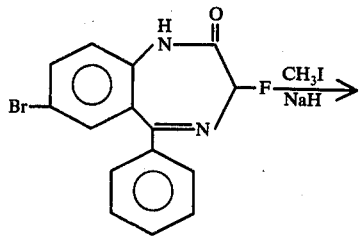

A slurry of 0.34 g (0.014 mole) of sodium hydride in 20 ml of tetrahydrofuran was added to a solution of 4.0 g (0.012 mole) of 7-bromo-1,3-dihydro-3-fluoro-5-phenyl-2H-1,4-benzodiazepin-2-one and 13 ml methyl iodide in 125 ml of tetrahydrofuran. The reaction mixture was stirred for 2.5 hr at room temperature (25°) and then poured into 600 ml of water containing 200 ml of methylene chloride. The organic layer was separated, washed with water, dried (MgSO$_4$), and evaporated to dryness to give 3.4 g of yellow residue. Recrystallization from cyclohexane gave 1.50 g of 7-bromo-1,3dihydro-3-fluoro-1-methyl-5-phenyl-2H-1,4-benzodiazepin-2-one as an amorphous cream-colored solid (no distinct melting point): $^1$H nmr (CDCl$_3$) δ 3.46 ppm (s, 3H), 5.60 ppm (d, J = 57 Hz, 1H), 7.2–7.9 ppm (m, 8H); $^{19}$F nmr (CDCl$_3$) δ −161.7 ppm (d, J = 57 Hz).

Anal. Calcd for C$_{16}$H$_{12}$BrFN$_2$O: C, 55.35; H, 3.49; F, 5.47. Found: C, 55.62; H, 3.72; F, 5.30; N, 7.97.

EXAMPLE 9

3-Fluoro-7-bromo-5-(2-fluorophenyl)-1,3-dihydro-2H-1,4-benzodiazepin-2-one

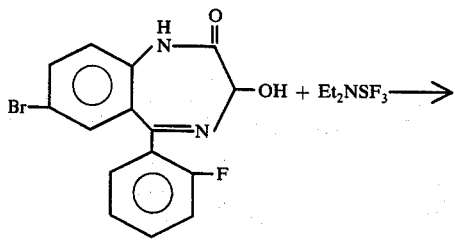

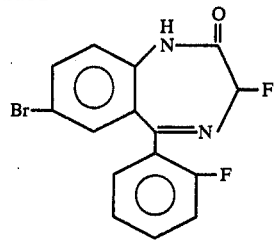

A stirred suspension of 4.2 g (0.012 mole) of 7-bromo-5-(2-fluorophenyl)-1,3-dihydro-3-hydroxy-2H-1,4-benzodiazepin-2-one in 200 ml methylene chloride was cooled to −70°, and 5 ml (0.04 mole) of diethylaminosulfur trifluoride was added dropwise. The reaction mixture was allowed to warm to −10°, and held at this temperature until most of the solid had dissolved. The reaction mixture was poured into icewater and stirred vigorously. The organic layer was separated, washed with water, dried (MgSO$_4$) and evaporated to dryness under reduced pressure. The residue was recrystallized from benzene-hexane to give 3.12 g of 3-fluoro-7-bromo-5-(2-fluorophenyl)-1,3-dihydro-2H-1,4-benzodiazepin-2-one as light yellow crystals: mp 195°–197° (dec.); $^{19}$F nmr (DMSO-d$_6$) δ −113.0 ppm (m, 1F) and −162.1 ppm (d, J = 56 Hz, 1F); $^1$H nmr (DMSO-d$_6$) δ 5.88 ppm (d, J = 56 Hz, 1H), 7.2–7.9 ppm (m, 7H), 11.2 ppm (NH).

Anal. Calcd for C$_{15}$H$_9$BrF$_2$N$_2$O: C, 51.30; H, 2.58; F, 10.81; N, 7.98. Found: C, 51.50; H, 2.69; F, 10.53; N, 8.05.

The 7-bromo-5-(2-fluorophenyl)-1,3-dihydro-3-hydroxy-2H-1,4-benzodiazepin-2-one used in this preparation was prepared by the following procedure.

A 9.5-g (0.027 mole) portion of 7-bromo-5-(2-fluorophenyl)-1,3-dihydro-2H-1,4-benzodiazepin-2-one 4-oxide was added portion-wise to 50 ml of trifluoroacetic anhydride, and the reaction mixture was stirred for 90 minutes. The suspended solid that formed was collected on a filter, washed thoroughly with pentane and dried in a vacuum over KOH. There was obtained 9.72 g (80%) of 7-bromo-5-(2-fluorophenyl)-1,3-dihydro-3-trifluoroacetoxy-2H-1,4-benzodiazepin-2one as an off-white crystalline powder: mp 175°–177° (dec.); $^{19}$F nmr (DMSO-d$_6$) δ −74.6 ppm (s, 3F) and −112.7 ppm (m, 1F); $^1$H nmr (DMSO-d$_6$) δ 6.34 ppm (s, 1H), 7.1–8.1 ppm (m, 7H), 11.5 ppm (NH).

Anal. Calcd for C$_{17}$H$_9$BrF$_4$N$_2$O$_3$: C, 45.86; H, 2.04; F, 17.70; N, 6.29. Found: C, 44.55; H, 1.91; F, 18.00; N, 6.31.

A suspension of 9.5 g (0.021 mole) of 7-bromo-5-(2-fluorophenyl)-1,3-dihydro-3-trifluoroacetoxy-2H-1,4-benzodiazepin-2-one in a mixture of 130 ml ethanol and 130 ml aqueous 5% sodium bicarbonate was stirred at 25° for 18 hr. The suspended solid was collected on a filter, washed with water, dried in air, and recrystallized from ethanol to give 4.54 g (62%) 7-bromo-5-(2-fluorophenyl)-1,3-dihydro-3-hydroxy-2H-1,4-benzodiazepin-2-one as colorless crystals: mp 196°–198°; $^{19}$F nmr (DMSO-d$_6$) δ −113.5 ppm (m); $^1$H nmr (DMSO-d$_6$) δ 4.88 ppm (s, 1H), 6.35 ppm (s, OH), 7.0–7.9 ppm (m, 7H).

Anal. Calcd for C$_{15}$H$_{10}$BrFN$_2$O$_2$: C, 51.59; H, 2.89; F, 5.44; N, 8.02. Found: C, 51.63; H, 2.97; F, 5.41; N, 7.89.

EXAMPLE 10

3-Fluoro-7-bromo-5-(2-fluorophenyl)-1,3-dihydro-1-methyl-2H-1,4-benzodiazepin-2-one

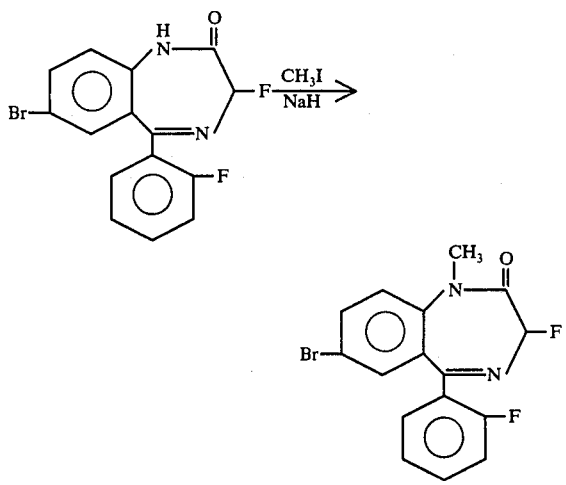

A slurry of 0.17 g (0.007 mole) of sodium hydride in 10 ml of tetrahydrofuran was added to a solution of 1.8 g (0.005 mole) of 3-fluoro-7-bromo-5-(2-fluorophenyl)-1,3-dihydro-2H-1,4-benzodiazepin-2-one and 10 ml methyl iodide in 100 ml tetrahydrofuran. The reaction mixture was stirred for 3 hr at 25° and then poured into 300 ml ice water. The aqueous mixture was extracted with methylene chloride, and the extracts were dried (MgSO₄) and then evaporated to dryness under reduced pressure. The residue was recrystallized from heptane to give 0.91 g (50%) of cream-colored crystals: mp 127°–130° (with previous softening); ¹H nmr (CDCl₃) δ 3.49 ppm (s, 3H), 5.62 ppm (d, J = 57 Hz, 1H) and 6.9–7.9 ppm (m, 7H); ¹⁹F nmr (CDCl₃) δ −111.9 ppm (m, 1F) and −162.4 ppm (d, J = 57 Hz, 1F).

Anal. Calcd for $C_{16}H_{11}BrF_2N_2O$: C, 52.62; H, 3.04; F, 10.41; N, 7.67. Found: C, 52.49; H, 3.30; F, 10.31; N, 7.57.

EXAMPLE 11

3-Fluoro-7-chloro-5-(2-chlorophenyl)-1,3-dihydro-2H-1,4-benzodiazepin-2-one

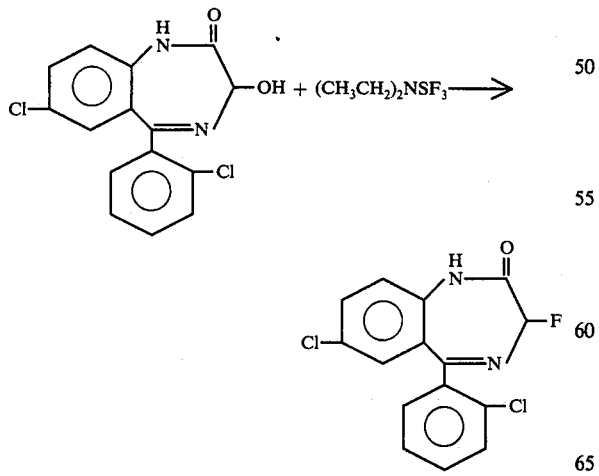

A well-stirred suspension of 6.8 g (0.021 mol) 8-chloro-5-(2-chlorophenyl)-3-hydroxy-1,3-dihydro-2H-1,4-benzodiazepin-2-one in 350 ml methylene chloride was cooled to −72° under nitrogen. Diethylaminosulfur trifluoride (10.5 ml, 0.80 mol) was added dropwise over a period of 10 min. at −72° to −70°. The suspension was allowed to warm slowly to −10° and held at −10° for 30 min., then poured into 500 ml ice water with vigorous stirring. The organic layer was separated, dried over MgSO₄ and evaporated, yielding 7.8 g of orange-yellow solid. The product was dissolved in benzene and allowed to crystallize, yielding 3.59 g of white crystalline 8-chloro-5-(2-chlorophenyl)-3-fluoro-3H-1,4-benzodiazepin-5-one: mp 210°–211° (dec.); 95% pure by high pressure liquid chromatography and UV analysis. A second crop (1.7 g) was obtained by addition of n-hexane. ¹H nmr (DMSO-d₆) δ 11.3 ppm (m, 1H), δ 7.5 ppm (m, 6H), 7.03 ppm (d, 1H), δ 5.92 ppm (d, J = 56 Hz, 1H); ¹⁹F nmr (DMSO-d₆) δ −162.3 ppm (d, J = 56 Hz, to d, J = 4 Hz).

EXAMPLE 12

3-Fluoro-7-chloro-5-(2-chlorophenyl)-1,3-dihydro-1-methyl-2H-1,4-benzodiazepin-2-one

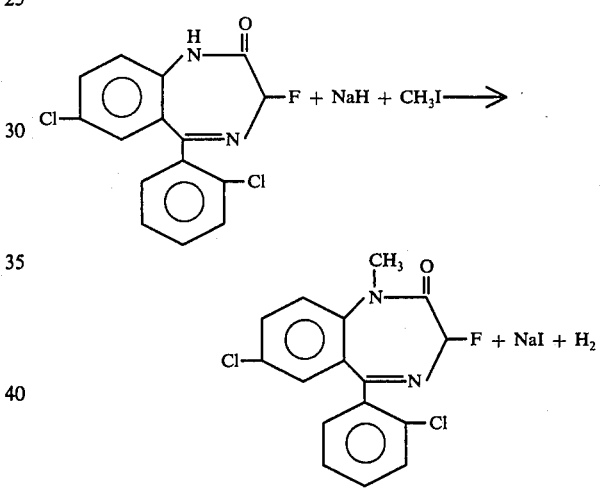

Sodium hydride (0.25 g of 50% mineral oil emulsion washed twice with tetrahydrofuran, 0.0050 mole) in 10 ml tetrahydrofuran was added portionwise at ambient temperature to a well stirred solution of 1.7 g (0.0053 mole) 3-fluoro-7-chloro-5-(2-chlorophenyl)-1,3-dihydro-2H-1,4-benzodiazepin-2-one and 5.6 g (0.039 mole) methyl iodide in 50 ml tetrahydrofuran under nitrogen. The solution was stirred 2 hr at room temperature, then poured into 100 ml water. The product was extracted with methylene chloride, the extract dried over MgSO₄ and the solvent evaporated, yielding a tan solid. The crude product was dissolved in benzene and allowed to crystallize giving a white solid; a second crop was obtained by addition of n-hexane, yielding a total of 1.1 g of 3-fluoro-8-chloro-5-(2-chlorophenyl)-1,3-dihydro-1-methyl-2H-1,4-benzodiazepin-2-one: mp 204°–205°; ¹H nmr (DMSO-d₆) δ 7.6 ppm (m, 6H), δ 7.0 ppm (m, 1H), δ 5.94 ppm (d, 56 Hz, 1H), δ 3.45 ppm (s, 3H); ¹⁹F nmr (DMSO-d₆) δ −161.8 ppm (d, J = 56 Hz).

Anal. Calcd for $C_{16}H_{11}N_2OCl_2F$: C, 56.99; H, 3.29; N, 8.31; Cl, 21.03; F, 5.63. Found: C, 57.11; H, 3.54; N, 8.37; Cl, 20.84; F, 5.69.

EXAMPLE 13

3-Fluoro-1,3-dihydro-7-nitro-5-phenyl-2H-1,4-benzodiazepin-2-one

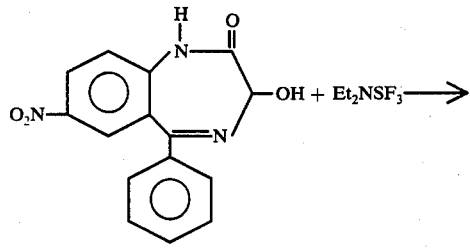

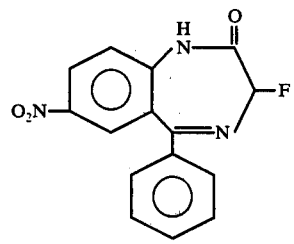

A well stirred suspension of 3.6 g (0.012 mole) of 1,3-dihydro-3-hydroxy-7-nitro-5-phenyl-2H-1,4-benzodiazepin-2-one in 200 ml methylene chloride was cooled to −70°, and 5 ml (0.04 mole) of diethylaminosulfur trifluoride was added dropwise. The reaction mixture was allowed to warm slowly to −10°, at which temperature all of the solid went into solution. The reaction mixture was poured into 400 ml of ice water, and the organic layer was separated, washed with water, dried (MgSO$_4$) and evaporated to dryness under reduced pressure. The residue was recrystallized from benzene-heptane to give 3.0 g (83%) of 3-fluoro-1,3-dihydro-7-nitro-5-phenyl-2H-1,4-benzodiazepin-2-one as colorless crystals: mp 174°–175° (dec.); $^1$H nmr (DMSO-d$_6$) δ 5.90 ppm (d, J = 57 Hz, 1H), 7.3–7.7 ppm (m, 6H), 8.07 ppm (d, J = 2.5 Hz, 1H) and 8.45 ppm (d, d, J = 9.0, 2.5 Hz, 1H); $^{19}$F nmr (DMSO-d$_6$) δ −161.4 ppm (d, J = 57 Hz).

Anal. Calcd for C$_{15}$H$_{10}$FN$_3$O$_3$: C, 60.20; H, 3.37; F, 6.35; N, 14.04. Found: C, 60.02; H, 3.43; F, 6.21; N, 13.88.

EXAMPLE 14

3-Fluoro-1,3-dihydro-1-methyl-7-nitro-5-phenyl-2H-1,4-benzodiazepin-2-one

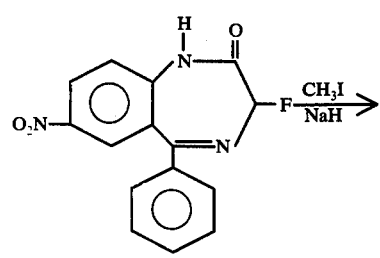

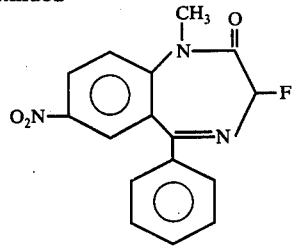

A slurry of 0.20 g (0.08 mole) of sodium hydride in 10 ml of tetrahydrofuran was added to a solution of 1.74 g (0.0058 mole) of 3-fluoro-1,3-dihydro-7-nitro-5-phenyl-2H-1,4-benzodiazepin-2-one and 10 ml methyl iodide in 100 ml of tetrahydrofuran at 25°. The reaction mixture was stirred for 3 hr at 25°, and then poured into 300 ml of ice water. The aqueous mixture was extracted with methylene chloride, and the extracts were dried (MgSO$_4$) and then evaporated to dryness under reduced pressure. The residue was dissolved in hot benzene and then fractionally precipitated by the addition of hexane. The first dark fractions of solid were discarded. The remaining fractions were collected on a filter and dried in vacuum to give 1.10 g (60%) of 3-fluoro-1,3-dihydro-1-methyl-7-nitro-5-phenyl-2H-1,4-benzodiazepin-2-one as a light tan amorphous solid with no distinct melting point: $^1$H nmr (CDCl$_3$) δ 3.53 ppm (s, 3H), 5.59 ppm (d, J = 57 Hz, 1H), 7.2–7.9 ppm (m, 6H) and 8.2–8.9 ppm (m, 2H); $^{19}$F nmr (CDCl$_3$) δ −161.7 ppm (d, J = 57 Hz).

EXAMPLE 15

3-Fluoro-7-chloro-1,3-dihydro-N-methyl-2-oxo-5-phenyl-2H-1,4-benzodiazepine-1-carboxamide

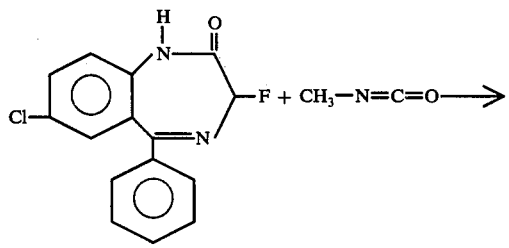

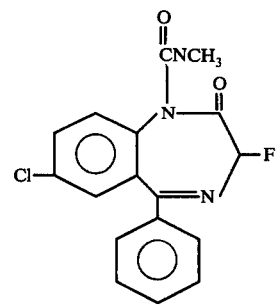

A stirred mixture of 3.56 g (0.12 mol) of 3-fluoro-7-chloro-1,3-dihydro-5-phenyl-2H-1,4-benzodiazepin-2-one, 35 ml of benzene and 1.06 g (0.019 mol) of methyl isocyanate was refluxed slowly for approximately 20 hours. The cool mixture was evaporated to dryness under reduced pressure to give 4.42 g of crude product as a light beige powder. Recrystallization from approximately 100 ml of hot ethanol gave 1.99 g of a white powder (mp 224°–225°) identified as 3-fluoro-7-chloro-1,3-dihydro-N-methyl-2-oxo-5-phenyl-2H-1,4-benzodiazepine-1-carboxamide: $^1$H nmr (CDCl$_3$) δ 8.4–8.7 ppm (1H, N—H, broad quartet); δ 7.25–8.0 (8H, m, aromatic); δ 5.72 (1H, d, J = 56.5 Hz); δ 2.93 (3H, d, J = 4.5 Hz, N—CH$_3$). $^{19}$F nmr (CDCl$_3$) δ −160.75 ppm (J = 57 Hz).

Anal. Calcd for C$_{17}$H$_{13}$N$_3$ClO$_2$F: C, 59.05; H, 3.79; N, 12.15; F, 5.49. Found: C, 59.01; H, 4.00; N, 11.69; F, 5.28.

EXAMPLE 16

3-Fluoro-7-chloro-1,3-dihydro-N-ethyl-2-oxo-5-phenyl-2H-1,4-benzodiazepine-1-carboxamide

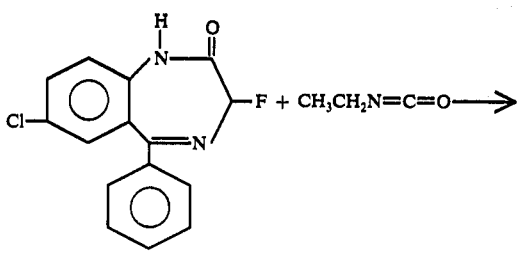

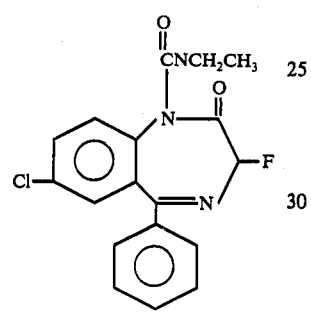

A stirred mixture of 3.56 g (.012 mol) of 3-fluoro-7-chloro-1,3-dihydro-5-phenyl-2H-1,4-benzodiazepin-2-one, 35 ml of benzene and 1.29 g (0.018 mol) of ethylisocyanate was refluxed slowly for about 20 hours. A suspended insoluble solid was removed from the cool mixture by filtration. The filtrate was then evaporated to dryness under reduced pressure to give 1.92 g of a yellow glassy material. Recrystallization from approximately 100 ml of cyclohexane gave 0.90 g of an off-white powder (mp 110°–112°) identified as 3-fluoro-7-chloro-1,3-dihydro-N-ethyl-2-oxo-5-phenyl-2H-1,4-benzodiazepine-1-carboxamide: $^1$H nmr (CDCl$_3$): δ 1.2 ppm (t, 3H, J = 7 Hz), δ 3.1–3.68 (dg, 2H), δ 5.67 (d, 1H, J = 57 Hz), δ 7.2–8.0 (aromatic), δ 8.7 (N—H). $^{19}$F nmr (CDCl$_3$): δ −160.67 ppm (d, J = 57 Hz).

EXAMPLE 17

4-Fluoro-8-chloro-1-methyl-6-phenyl-4H-s-triazolo[4.3-a]-[1.4]benzodiazepine

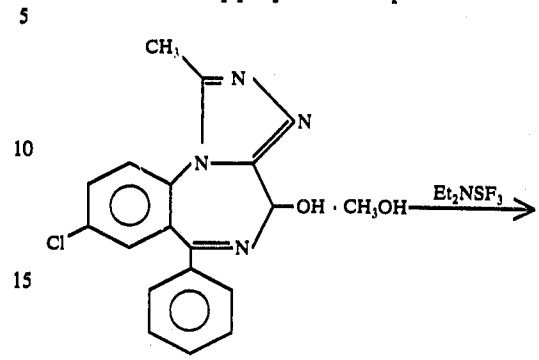

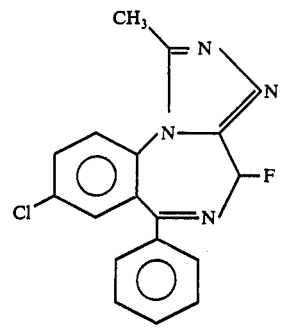

A solution of 5.0 g (0.014 mole) of 8-chloro-4-hydroxy-1-methyl-4H-s-triazolo[4.3-a][1,4]benzodiazepine methanol solvate in 250 ml methylene chloride was cooled to −70°, and 10 ml of diethylaminosulfur trifluoride was added over a period of 10 min. The reaction mixture was warmed over 20 min. to −20°, held at −20° for 20 min., and then poured into 500 ml of ice water. The aqueous mixture was neutralized with sodium bicarbonate, and the organic layer was separated, washed with water, dried (MgSO$_4$), and evaporated to dryness to give 4.1 g of 4-fluoro-8-chloro-1-methyl-6-phenyl-4H-s-triazolo[4.3-a]-[1,4]-benzodiazepine: mp 232°–235° (dec.); $^{19}$F nmr (DMSO-d$_6$) δ −167.1 ppm (d, J = 52 Hz); $^1$H nmr (DMSO-d$_6$) δ 2.62 ppm (s, 3H), 6.71 ppm (d, J = 52 Hz, 1H), 7.3–8.1 ppm (m, 8H).

The 4-hydroxy compound used in this preparation can be prepared as described in U.S. Pat. No. 3,907,820 (1975) (assigned to Takeda Chemical Industries, Ltd.).

Table 1 shows additional compounds that can be made using the appropriate 3-hydroxy starting material in the general method.

Table 1

| 3-Hydroxybenzo-diazepinone | Dialkylamino-sulfur Trifluoride | 3-Fluorobenzo-diazepinone |
|---|---|---|
|  | (C$_2$H$_5$)$_2$NSF$_3$ |  |

Table 1-continued

| 3-Hydroxybenzo-diazepinone | Dialkylamino-sulfur Trifluoride | 3-Fluorobenzo-diazepinone |
|---|---|---|
| | $(C_2H_5)_2NSF_3$ | |
| | $\underset{\smile}{N}NSF_3$ (pyrrolidine) | |
| | $(C_2H_5)_2NSF_3$ | |
| | $\underset{\smile}{N}NSF_3$ (piperidine) | |
| | $(C_2H_5)_2NSF_3$ | |
| | $(CH_3)_2NSF_3$ | |

Table 1-continued

| 3-Hydroxybenzo-diazepinone | Dialkylamino-sulfur Trifluoride | 3-Fluorobenzo-diazepinone |
|---|---|---|
| [3-hydroxy-1-(2,3-epoxypropyl)-7-chloro-5-phenyl-benzodiazepinone structure] | $(C_2H_5)_2NSF_3$ | [3-fluoro-1-(2,3-epoxypropyl)-7-chloro-5-phenyl-benzodiazepinone structure] |

Table 2 shows additional compounds that can be made by the alternate method using the appropriate fluorobenzodiazepinone.

Table 2

| 1-Unsubstituted Benzodiazepinone | Alkylating Reagent | 1-Substituted Benzodiazepinone |
|---|---|---|
| [7-chloro-3-fluoro-5-phenyl-benzodiazepinone, 1-H] | $BrCH_2CH_2CH_2CH_3$ | [1-butyl-7-chloro-3-fluoro-5-phenyl-benzodiazepinone] |
| [7-nitro-3-fluoro-5-phenyl-benzodiazepinone, 1-H] | $CF_3CH_2OSO_2CF_3$ | [1-(2,2,2-trifluoroethyl)-7-nitro-3-fluoro-5-phenyl-benzodiazepinone] |
| [7-chloro-3-fluoro-5-phenyl-benzodiazepinone, 1-H] | $ClCH_2CH_2N(C_2H_5)_2$ | [1-(2-diethylaminoethyl)-7-chloro-3-fluoro-5-phenyl-benzodiazepinone] |
| [7-trifluoromethyl-3-fluoro-5-(2-chlorophenyl)-benzodiazepinone, 1-H] | $CH_3I$ | [1-methyl-7-trifluoromethyl-3-fluoro-5-(2-chlorophenyl)-benzodiazepinone] |

Table 2-continued

| 1-Unsubstituted Benzodiazepinone | Alkylating Reagent | 1-Substituted Benzodiazepinone |
|---|---|---|

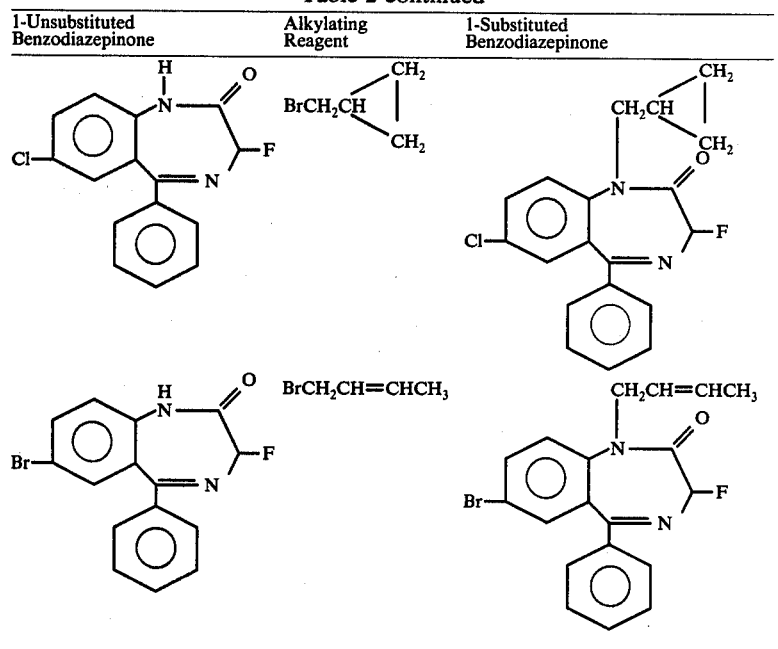

Table 3 shows additional 4-fluorotriazolobenzodiazepines that can be made using the appropriate 4-hydroxy starting material.

TABLE 3

| 4-Hydroxytriazolo-benzodiazepine | Dialkylamino-Sulfur Trifluoride | 4-Fluorotriazolo-benzodiazepine |
|---|---|---|

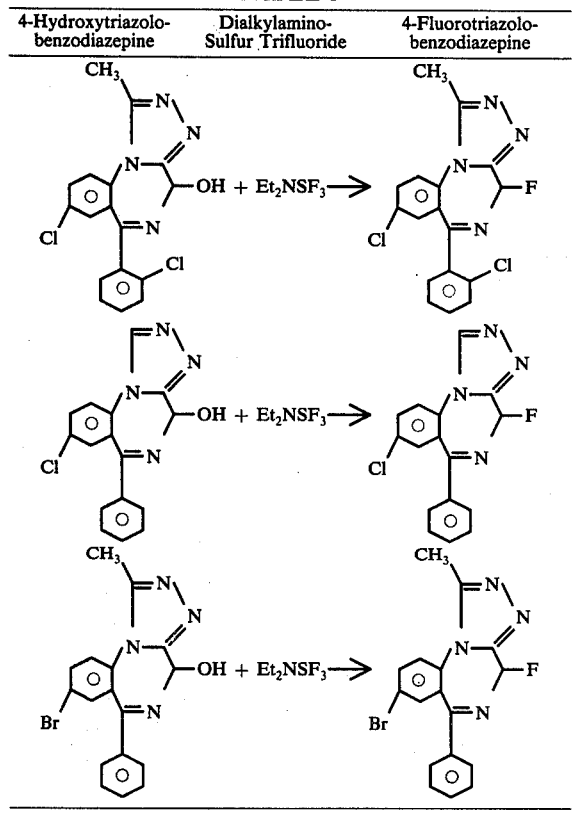

Dosage Forms

The tranquilizers, muscle relaxants, and sedatives of this invention can be administered to produce the desired effect by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 100 milligrams per kilogram of body weight. Ordinarily 0.01 to 50, and preferably 0.05 to 25 milligrams per kilogram per day given in divided doses 2 to 4 times a day or in sustained release form is effective to obtain desired results.

Dosage forms (compositions) suitable for internal administration contain from about 0.1 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; and water-soluble class includes polyethylene glycols.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 2.0 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 1 milligram of the active ingredient. The capsules are washed in petroleum ether and dried.

Tablets

A large number of tablets are prepared by conventional procedures so that the dosage unit is 0.5 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 0.5 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

Utility

Standard procedures for detecting and comparing the tranquilizer, muscle-relaxant, and sedative activity of compounds in this series for which there is a correlation with human efficacy are the following: pinna reflex tests, antipentylenetetrazole test, rat activity suppression test (RAST), muscle relaxant (anti-straub tail) test, and mouse activity suppression test (MAST).

PINNA REFLEX TESTS

Fasted female white mice, 5 per dose are intubated with drug at 4, 12, 36, 108 and 324 mg/kg in 1% Methocel®- 1.25% Tween 80®, at 10 ml/kg. The auditory and tactile pinna are tested at 0.5, 2, 5 and 24 hours.

Auditory Pinna Reflex

The mouse is placed on a horizontal bar 9 cm from a Galton whistle adjusted for 13 Kc. Failure to flatten the ears during one or 2 short bursts of sound constitutes loss of auditory pinna reflex.

Tactile Pinna Reflex

The mouse is held by the tail and the hairs inside the right ear are touched by the fine wire stylus from a 27 gauge needle. Failure of the mouse to twitch or move the head constitutes loss of the tactile pinna reflex.

ANTIPENTYLENETETRAZOLE (PTZ) TEST

Fasted female white mice, 10 per dose are intubated with drug in vehicle as above at doses such as 0, 1, 3, 9, 27 and 81 mg/kg. Thirty minutes later the mice are dosed intravenously with PTZ (Metrazol®[1]) at 40 mg/kg (ED98 for clonic convulsions). Dosed animals which remain on a 4" × 4" platform for 20 seconds are considered protected. Quantal $ED_{50}$'s are calculated by the moving average method.

[1] Original brand of pentylenetetrazole; sterile 10% aqueous solution for parenteral injection, Knoll Pharmaceutical Company.

RAT ACTIVITY SUPPRESSION TEST (RAST)

The test apparatus consists of a circular cage with lid and with a floor of electrifiable steel bars. D.C. shock current is supplied to the bars such that touching any 2 alternate bars shocks the rat. The floor is marked to yield 4 equal pie-shaped sectors.

Fasted male white rats, 10 per dose are intubated with drug as described above for mice. Thirty minutes after dosing a rat is placed in the test apparatus and is allowed 30 seconds to transverse 25% of the floor area after which he receives a shock. The rat is allowed 5 seconds to recover from the shock, then its "line crossings" are counted for 60 seconds. The mean number of crossings per rat for each dose are determined and are compared to the mean number of crossings of the vehicle treated controls. $ED_{50}\%$, the dose which would increase the number of crossings 50% over controls, is determined graphically.

MUSCLE RELAXANT (ANTI-STRAUB TAIL) TEST

Fasted female white mice, 5 per dose are intubated with test drug. Twenty-five minutes later morphine sulfate is given subcutaneously at 53.7 mg/kg. Thirty minutes after test drug the mice are observed for presence of Straub tail. Quantal $ED_{50}$ values for blockade of morphine-induced Straub tail are calculated.

MOUSE ACTIVITY SUPPRESSION TEST (MAST)

The Mouse Activity Suppression Test (MAST) is a model system designed to detect compounds with possible anti-anxiety activity in humans. The test is based upon punishment of mice for exhibiting normal exploratory locomotor behavior. The punishment, an electric shock applied through the mouse's paws, quickly extinguishes normal behavior. Pretreatment with a minor tranquilizer prevents or delays the extinction, while major tranquilizers, analgesics, stimulants, anti-depressants, antihistaminics, and purely sedative drugs are inactive.

The test procedure is modified from Boissier, et al., European J. Pharm., 4, 145-151 (1968). Female white mice, fasted 16-22 hours, are randomly distributed to fiberglass holding boxes. Mice in groups of 10-20 are dosed orally and returned to their holding boxes until test time. Test drug suspensions or solutions are prepared by sonication in 1% Methocel ®. Typical dose ranges include 0.5, 1, 2, and 4 mg/kg or 1, 3, 9, 27, 81 mg/kg plus a vehicle control and are selected to include one dose at which an effect such as sedation, stimulation, muscle weakness or analgesia was seen.

The test apparatus is an opaque, black plastic box with a clear lid and a stainless steel grid floor. The floor of the test box is marked off into four squares of equal size.

After dosing, a mouse is gently place in one corner of the testing box and during the next minute each time the mouse makes a full crossing from one square section of the box to another the floor is electrified with 0.4 ma current for 2.0 seconds.

The number of shocks received by each mouse is recorded and the mean number of shocks/dose ($\overline{X}$) is determined. When $\overline{X}$ drug at any dose is statistically greater than $\overline{X}$ controls (Student's $t$ test), antagonism of suppression obtains and the drug is presumed to have anti-anxiety activity.

Potency in the antipentylenetetrazole (PTZ), the MAST, and the RAST tests indicates a potent antianxiety agent. Great potency for blockade of the mouse auditory pinna reflex with little or no effect on tactile pinna reflex is characteristic of minor tranquilizers. Potency in the mouse anti-straub tail test suggests skeletal muscle relaxant activity.

The following table includes the results of these tests conducted with a representative sample of the compounds of this invention; it also includes the results for diazepam, oxazepam, and chlordiazepoxide, three well-known benzodiazepines widely-used commercially as tranquilizers.

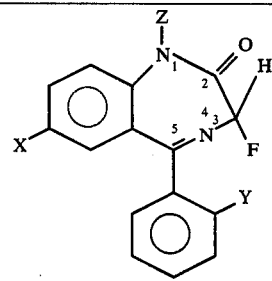

| Compound | X | Y | Z | MOUSE ED50 VALUES PINNA REFLUX Auditory | Tactile | ANTI-PTZ | MAST* | MUSCLE RELAXANT | RAT ED50% VALUES RAST |
|---|---|---|---|---|---|---|---|---|---|
| Diazepam[a] | Cl | H | —CH₃ | 4 | 187 | 0.49 | 1.1 | 1 | 1.5 |
| Oxazepam[b] | Cl | H | —H | 2.9 | | 2. | 2.7 | 0.26 | 2.5 |
| Chlordiazepoxide[c] | Cl | H | —H | 70 | 320 | 7.5 | 8.5 | 1.9 | 6. |
| | Cl | H | —H | 2.6 | | 0.39 | 0.37[d] | 0.10 | |
| | Cl | F | —H | 12 | 200 | 0.42 | 0.48 | — | |
| | Cl | Cl | —H | <4 | >324 | 0.34 | 1.15 | <0.33 | |
| | Cl | H | —CH₃ | 5 | 121 | 0.18 | 0.25 | 0.25 | 0.45 |
| | Cl | F | —CH₃ | 7 | 200 | 0.12 | 0.05 | 0.06 | 0.24 |
| | Cl | Cl | —CH₃ | 60 | >324 | 0.09 | | | |
| | Cl | H | —C₂H₅ | 12 | >324 | 0.56 | 0.45 | <0.24 | |
| | Cl | H | —CH₂CH=CH₂ | 20 | 100 | 6.1 | 2.9 | <1 | |
| | Cl | H | —C(O)NHCH₃ | <4 | 36 | | | | |
| | Br | H | —H | 1.2 | 100 | 0.74 | 0.04 | 0.05 | 0.15 |
| | Br | F | —H | <4 | 300 | 0.12 | | | |
| | Br | H | —CH₃ | 1.3 | 300 | 0.22 | 0.16 | | 1.7 |
| | Br | F | —CH₃ | <4 | <324 | 0.06 | | | |

[a] 3F replaced by 3H.
[b] 3F replaced by 3OH.
[c] No 3F, carbonyl replaced by NHCH₃ and → 0 on the 4N.
[d] At 60 minutes; all others were at 30 minutes.
*ED20%

We claim:

1. A Process for preparing a compound of the formula:

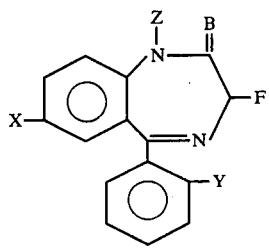

wherein
X is Cl, Br, NO$_2$ or CF$_3$;
Y is H, Cl, Br or F;
Z is H, hydrocarbyl of 1–4 carbons, —CH$_2$—CF$_3$, —COHNR, —CH$_2$—CH$_2$NR$_2$ or —CH$_2$CH$_2$NR$_2$·A, where R is alkyl of 1–4 carbons, and A is a pharmaceutically suitable acid;
B is O; or
B and Z together is =N—N=C(R')—where R' is H or C$_1$–C$_4$ alkyl which comprises:

contacting, under substantially anhydrous conditions at a temperature of about −80° to +10° C., a compound of the formula

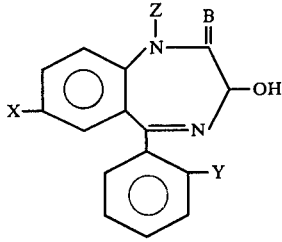

with a compound of the formula:

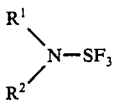

where B, X, Y and Z are as previously defined, and R$^1$ and R$^2$ individually are a primary alkyl group of 1–4 carbons or taken together are —(CH$_2$)$_4$— or —(CH$_2$)$_5$—.

* * * * *